US005744623A

United States Patent [19]
Garcia Gravalos et al.

[11] Patent Number: 5,744,623
[45] Date of Patent: Apr. 28, 1998

[54] TERPENE-QUINONES WITH ANTITUMOUR ACTIVITY

[75] Inventors: M$^a$ Dolores Garcia Gravalos, Madrid; Marina Gordaliza Escobar; Santana Jose M$^a$ Miguel Del Corral, both of Salamanca; M$^a$ del Mar Mahiques Bujanda, Alicante; Arturo San Feliciano Martin, Salamanca, all of Spain

[73] Assignee: Pharma Mar, s.a., Madrid, Spain

[21] Appl. No.: 624,593

[22] PCT Filed: Aug. 1, 1995

[86] PCT No.: PCT/ES95/00096

§ 371 Date: Oct. 4, 1996

§ 102(e) Date: Oct. 4, 1996

[87] PCT Pub. No.: WO96/04230

PCT Pub. Date: Feb. 15, 1996

[30] Foreign Application Priority Data

| Aug. 1, 1994 | [ES] | Spain | 9401697 |
| Apr. 27, 1995 | [ES] | Spain | 9500817 |

[51] Int. Cl.$^6$ .................................. C07C 221/00
[52] U.S. Cl. ................ 552/297; 552/298; 552/299; 568/609; 568/736
[58] Field of Search ............... 552/297, 298, 552/299; 568/609, 736

[56] References Cited

U.S. PATENT DOCUMENTS

| Re. 34,414 | 10/1993 | Okayaki et al. | 552/299 |
| 4,786,652 | 11/1988 | Venuti | 552/297 |
| 4,946,869 | 8/1990 | Muller et al. | 514/729 |
| 5,082,865 | 1/1992 | Muller et al. | 514/729 |
| 5,466,711 | 11/1995 | Latter et al. | 552/298 |

FOREIGN PATENT DOCUMENTS

| WO 950423A1 | 2/1996 | WIPO . |

OTHER PUBLICATIONS

Sasaki, T. et al. Studies on Reactions of Isoprenoids. Journal of Organic Chemistry. Dec. 1969, vol. 34, No. 12, pp. 3749–3753.

Alves Da Silva, et al. Biological Activity of Cordialquinones . . . Fitoterapia 1993, vol. 64, No. 1 pp. 78–81.

Bieber, L.W., et al. Meroterpenoid Napthoquinones From Cordia Corymbosa, Phytochen. 1990, vol. 29, No. 6, pp. 1955–1959.

Bieber, L.W., et al. Further Meroterpenoid Napthoquinones From Cordia Corymbosa, Phytochen. 1994, vol. 35, No. 4, pp. 1027–1028.

Rodriguez et al. The Structures and Sterochem of Cytotoxic Sesquiterpene Quinones from *Dactylospongia Elegans*, 1992 vol. 48, No. 32, pp. 6667–6680.

Sasaki et al. J. Org. Chem., vol. 34, pp. 3749–3752 (1969).

Bieber et al(I), Phytochemistry, vol. 35, pp. 1027–1028 (1994).

Bieber et al(II) Phytochemistry, vol. 29, pp. 1959–9 (1990).

Klac et al. Chem. Abstr., vol. 107, #197, 697q (1987).

*Primary Examiner*—James H. Reamer
*Attorney, Agent, or Firm*—Ernest V. Linek

[57] ABSTRACT

Terpene-quinone with antitumor activity defined from a cyclocondensation reaction of Diels-Alder, used to obtain families or series of said compounds having a new structure and presenting a cytotoxic activity to cellular cultures P-388, A-549, HT-29 and MEL-28, with levels of IC$_{50}$ lower than 1 microgram per unit of milliliter.

27 Claims, No Drawings

TERPENE-QUINONES WITH ANTITUMOUR ACTIVITY

Present document relates to the developement of a series of novel products such as a new series of terpene-quinones, as well as the procedure for its obtention.

Avarol and its quinone analogue, avarone are merosequiterpenoids isolated from a sponge, *Dysidea avara*, which showed certain cytotoxic activity and which can be considered as a model for a series of analogous, yet discovered or prepared afterwards, containing different variants of substitution at the quinone portion and/or the chain at the sesquiterpene portion. A good number of these compounds containing a bicyclic serterpene system posess cytotoxic activity with values of $IC_{50}$ arround 1 microgram per millilitre. Other sesquiterpene-quinones with monocyclic terpene groups have also similar levels of activity.

Up to date, there has not been published any study on the structure-activity relationship of these compounds regarding to size and type of quinone and terpene groups of the molecule. Therefore, in this work it has been aimed to analyze the effect of the increase, diminution and functionalization of terpene group and the expansion of quinone nucleus up to naphthoquinone.

In order to realize a clear exposition of the processes of the invention, it will be attached to this text those reactions which are going to be explained hereinafter, written as their chemical formulae, said reactions resulting the invention's generic ones.

The molecules which are the objective or this work comprise a simple or substituted type A naphthoquinone as quinone system, in which $R^1$ is an alkyl or alkoxy group and T matches an alkyl or cycloalkyl group, prefferably of isoprene, monoterpene, sesquiterpene type or with an intermediate size between these types.

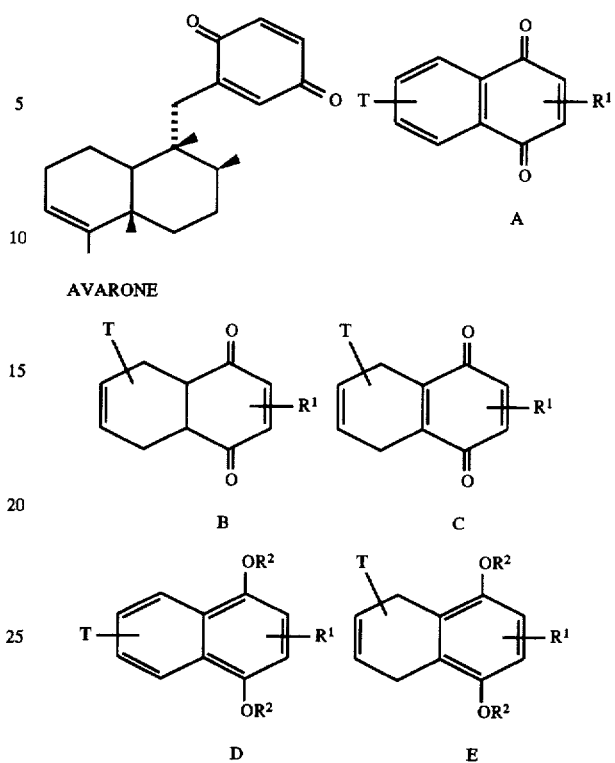

AVARONE

Likewise, there are included as an objective those naphthoquinone derivatives of types B and C and the corresponding dihydroxynaphthalene analogous of types D and E.

Most of these compounds have been synthetized by using the Diels-Alder cyclocondensation, as a base-reaction, between conveniently substituted p-benzoquinone and a compound comprising a conjugated diene system, in the presence of a catalyst or not. The further Manipulation, equilibration or chemical modification of the directly resulting cycloaddition product (B) can successively yield the compounds of types E, C, D and A which are represented below for two different kinds of diene system substitution.

This first kind of diene system substitution is shown in its reaction as follows:

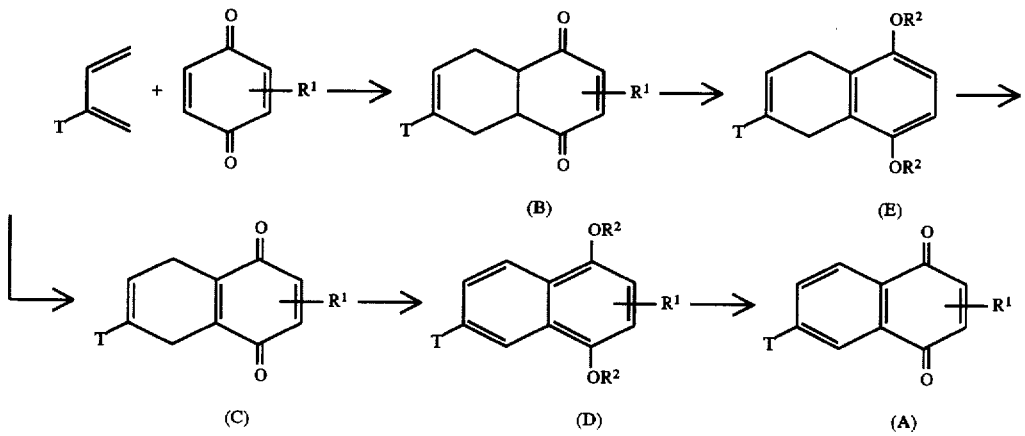

The second kind of diene system substitution fore mentioned will be:

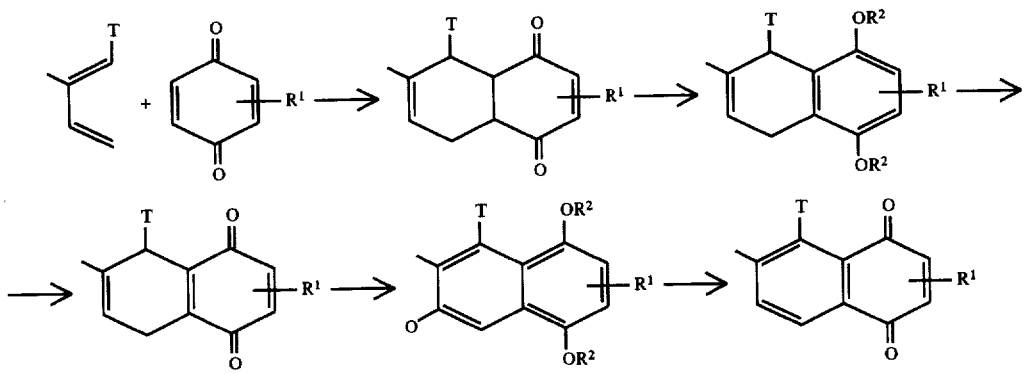

Starting compounds, useful for cycloadditions, have a conjugated diene system along carbon chains of the linear or branched alkane: 2,6-dimethyloctane, 2,6,10-trimethyldodecane, 2,6,10,14-tetramethylhexanedecane, 2,6,10,15,19,23-hexamethyltetracosane or on any other of a cyclical nature biogenesically or artificially related to these.

Chemical names of those kinds of compounds refered in said generic reactions will be the following, taking into consideration that in said names there will appear numbers and words in brackets, meaning possible positions for a substituent and the possibility for said function or structural modification to exist, respectively, and that they will be included in subtypes, depending on $R^1$ and T:

TYPE A COMPOUND $R^1$ =Hydrogen 5(6)-alkyl(alkenyl)-naphtho-1,4-quinones 5(6)-(poly)cycloalkyl(cycloalkenyl)-alkyl-naphtho-1,4-quinones 5(6) -(poly)cyclo(poly)isoprenyl-naphtho-1,4-quinones $R^1$=Alkyl 2(3)-alkyl-5(6)(7)(8)-alkyl(alkenyl)-naphtho-1,4-quinones 2(3)-alkyl-5(6)(7)(8)-(poly)cycloalkyl (cycloalkenyl)-alkyl-naphtho-1,4-quinones 2(3)-alkyl-5(6)(7)(8)-(poly)cyclo(poly)isoprenyl-naphtho-1,4-quinones $R^1$=Alkoxy 2(3)-alkoxy-5(6)(7)(8)-alkyl(alkenyl)-naphtho-1,4-quinones 2(3)-alkoxy-5(6)(7)(8)-(poly) cycloalkyl(cycloalkenyl)-alkyl-naphtho-1,4-quinones 2(3)-alkoxy-5(6)(7)(8)-(poly)cyclo(poly)isoprenyl-naphtho-1,4-quinones $R^1$=(di)Alkylamine 2(3)-(di)Alkylamine-5(6)(7)(8)-alkyl (alkenyl)-naphtho-1,4-quinones 2(3) -(di)Alkylamine-5(6)(7)(8)-(poly)cycloalkyl(cycloalkenyl)-alkyl-naphtho-1,4-quinones 2(3)-(di)Alkylamine-5(6)(7)(8)-(poly)cyclo(poly)isoprenyl-naphtho-1,4-quinones

TYPE B COMPOUND $R^1$=Hydrogen 5(6)-alkyl(alkenyl)-4a,5,8,8a-tetrahydro-naphthalene-1,4-diones 5(6)-(poly)cycloalkyl(cycloalkenyl)-alkyl-naphthalene-1,4-diones 5(6)-(poly)cyclo(poly)isoprenyl-naphthalene-1,4-diones $R^1$=Alkyl 2(3) -alkyl-5(6)(7) (8)-alkyl(alkenyl)-4a,5,8,8a-tetrahydro-naphthalene-1,4-diones 2(3)-alkyl-5(6)(7)(8)-(poly)cycloalkyl(cycloalkenyl)-alkyl-4a,5,8,8a-tetrahydro-naphthalene-1,4-diones 2(3)-alkyl-5(6)(7)(8)-(poly)cyclo(poly)isoprenyl-4a,5,8,8a-tetrahydro-naphthalene-1,4-diones $R^1$=Alkoxy 2(3)-alkoxy-5(6)(7)(8)-alkyl(alkenyl)-4a,5,8,8a-tetrahydro-naphthalene-1,4-diones 2(3)-alkoxy-5(6)(7)(8)-(poly)cycloalkyl(cycloalkenyl)-alkyl-4a,5,8,8a-tetrahydro-naphthalene-1,4-diones 2(3)-alkoxy-5(6)(7)(8)-(poly)cyclo(poly)isoprenyl-4a,5,8,8a-tetrahydro-naphthalene-1,4-diones $R^1$=(di)Alkylamine 2(3)-(di)Alkylamine-5(6)(7)(8)-alkyl (alkenyl)-4a,5,8,8a-tetrahydro-naphthalene-1,4-diones 2(3)-di)Alkylamine-5(6)(7)(8)-(poly)cycloalkyl (cycloalkenyl)-alkyl-4a,5,8,8a-tetrahydro-naphthalene-1,4-diones 2(3)-(di) Alkylamine-5(6)(7)(8)-(poly)cyclo(poly)isoprenyl-4a,5,8, 8a-tetrahydro-naphthalene-1,4-diones

TYPE C COMPOUND $R^1$=Hydrogen 5(6)-alkyl(alkenyl)-5,8-dihydro-naphtho-1,4-quinones 5(6)-(poly)cycloalkyl(cycloalkenyl)-alkyl-5, 8-dihydro-naphtho-1,4-quinones 5(6)-(poly)cyclo(poly) isoprenyl-5,8-dihydro-naphtho-1,4-quinones $R^1$=Alkyl 2(3)-alkyl-5(6)(7)(8)-alkyl(alkenyl)-5,8-dihydro-naphtho-1,4-quinones 2(3)-alkyl-5(6)(7)(8)-(poly) cycloalkyl(cycloalkenyl)-alkyl-5,8-dihydro-naphtho-1,4-quinones 2(3)-alkyl-5(6)(7)(8)-(poly)cyclo(poly)isoprenyl-5,8-dihydro-naphtho-1,4-quinones $R^1$=Alkoxy 2(3)-alkoxy-5(6)(7)(8)-alkyl(alkenyl)-5,8-dihydro-naphtho-1,4-quinones 2(3)-alkoxy-5(6)(7)(8)-(poly)cycloalkyl(cycloalkenyl)-alkyl-5,8-dihydro-naphtho-1,4-quinones 2(3)-alkoxy-5(6)(7)(8)-(poly)cyclo(poly) isoprenyl-5,8-dihydro-naphtho-1,4-quinones $R^1$=(di)Alkylamine 2(3)-(di)Alkylamine-5(6)(7)(8)-alkyl (alkenyl)-5,8-dihydro-naphtho-1,4-quinones 2(3)-(di) Alkylamine-5(6)(7)(8)-(poly)cycloalkyl(cycloalkenyl)-alkyl-5,8-dihydro-naphtho-1,4-quinones 2(3)-(di) Alkylamine-5(6)(7)(8)-(poly)cyclo(poly)isoprenyl-5,8-dihydro-naphtho-1,4-quinones

TYPE D COMPOUND $R^1$=Hydrogen 5(6)-alkyl(alkenyl)-naphthalene-1,4-diols and their diacetates(diesthers). 5(6)-(poly)cycloalkyl (cycloalkenyl)-alkyl-naphthalene-1,4-diols and their diacetates(diesthers). 5(6) -(poly)cyclo(poly)isoprenyl-naphthalene-1,4-diols and their diacetates(diesthers).

$R^1$=Alkyl 2(3)-alkyl-5(6)(7)(8)-alkyl-naphthalene-1,4-diols and their diacetates(diesthers). 2(3)-alkyl-5(6)(7)(8)-(poly)cycloalkyl(cycloalkenyl)-alkyl-naphthalene-1,4-diols and their diacetates(diesthers). 2(3)-alkyl-5(6)(7)(8)-(poly) cyclo(poly)isoprenyl-naphthalene-1,4-diols and their diacetates(diesthers).

$R^1$=Alkoxy 2(3)-alkoxy-5(6)(7)(8)-alkyl(alkenyl)-naphthalene-1,4-diols and their diacetates(diesthers). 2(3)-alkoxy-5(6)(7)(8)-(poly)cycloalkyl(cycloalkenyl)-alkyl-naphthalene-1,4-diols and their diacetates (diesthers). 2(3) alkoxy-5(6)(7)(8)-(poly)cyclo(poly)isoprenyl-naphthalene-1,4-diols and their diacetates(diesthers).

R¹=(di)Alkylamine 2(3)-(di)Alkilamine-3(6) (7)(8)-alkyl (alkenyl)-naphthalene-1,4-diols and their diacetates (diesthers). 2 (3)-(di)Alkilamine-5(6)(7)(8)-(poly) cycloalkyl(cycloalkenyl)-alkyl-naphthalene-1,4-diols and their diacetates(diesthers). 2(3)-(di)Alkilamine-5(6)(7)(8)-(poly)cyclo(poly)isoprenyl-naphthalene-1,4-diols and their diacetates(diesthers).

TYPE E COMPOUND

R¹=Hydrogen 5(6)-alkyl(alkenyl)-5,8-dihydro-naphthalene-1,4-diols and their diacetates(diesthers). 5(6)-(poly)cycloalkyl(cycloalkenyl)-alkyl-5,8dihydro-naphthalene-1,4-diols and their diacetates(diesthers). 5(6)-(poly)cyclo(poly)isoprenyl-5,8-dihydro-naphthalene-1,4-diols and their diacetates(diesthers).

R¹=Alkyl 2(3)-alkyl-5(6)(7)(8)-alkyl(alkenil)-5,8-dihydro-naphthalene-1,4-diols and their diacetates (diesthers). 2(3)-alkyl-5(6)(7)(8)-(poly)cycloalkyl (cycloalkenyl)-alkyl-5,8-dihydro-naphthalene-1,4-diols and their diacetates (diesthers). 2(3)-alkyl-5(6)(7)(8)-(poly) cyclo(poly)isoprenyl-5,8-dihydro-naphthalene-1,4-diols and their diacetates (diesthers).

R¹=Alkoxy 2(3) -alkoxy-5(6)(7)(8)-alkyl(alkenyl)-5,8-dihydro-naphthalene-1,4-diols and their diacetates (diesthers). 2(3)-alkoxy-5(6)(7)(8)-(poly)cycloalkyl (cycloalkenyl)-alkyl-5,8-dihydro-naphthalene-1,4-dials and their diacetates(diesthers). 2(3)-alkoxy-5(6)(7)(8)-(poly) cyclo(poly)isoprenyl-5,8-dihydro-naphthalene-1,4-diols and their diacetates (diesthers).

R¹=(di)Alkylamine 2(3)-(di)Alkilamine-5(6)(7)(8)-alkyl (alkenyl)-5,8-dihydro-naphthalene-1,4-diols and their diacetates(diesthers). 2(3)-(di)Alkilamine-5 (6)(7)(8)-(poly) cycloalkyl(cycloalkenyl)-alkyl-5,8-dihydro-naphthalene-1, 4-diols and their diacetates(diesthers). 2(3)-(di)Alkilamine-5(6)(7)(8)-(poly)cyclo(poly)isoprenyl-5,8-dihydro-naphthalene-1,4-diols and their diacetates (diesthers).

With this list, types of compounds which result the objective of the work collected in this invention patent document become specified with a higher precission, being fitted in types and subtypes according to the fore-mentioned explanation, formulae and reactions.

With said reactions and generic compounds, certain examples for practical incorporations developed in the laboratory can be determined, the following rules having been taken in order to obtain the concrete compounds which will be hereinafter mentioned.

First Example

To a solution of 733 milligrams or 2.32 milliMole of methyl mirceocomunate or compound 1, in anhydrous ether, another dry ether solution of 251 milligrams or 2.32 milliMole of p-benzoquinone and a catalytic amount of BF₃-etherate were added on stirring under inert atmosphere. Mixture was kept at room temperature for 24 hours. Water was added and it was washed up to neutralization. It was dried (Na₂SO₄), filtered and distilled and a brown semisolid residue is obtained which is subjected to chromatography on silica-gel, so finally obtaining 127 milligrams (13%) of 6-[14-methoxy-14-oxo-drim-8(12)-en-11-il-methyl]-naphtho-1,4-quinone or compound number 2 and 560 milligrams (57%) of 5,8-dihydro-[14-methoxy-14-oxo-drim-8(12)-en-11-il-methyl]-naphthalene-1,4-diol or compound number 3. Acetylation of compound 3 under standard conditions leads to an additional compound 3a named 5,8-dihydro-[14-methoxy-14-oxo-drim-8(12)-en-11-il-methyl]-naphthalene-1,4-diol diacetate.

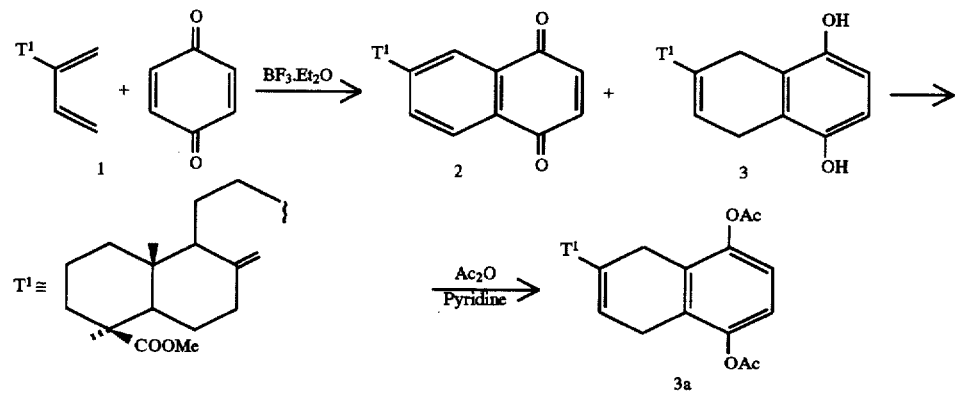

Second Example

From 450 milligrams or 1.42 milliMole of methyl mirceocomunate or compound 1, and 175 milligrams or 1.42 milliMole of 2-methyl-p-benzoquinone, in the presence of the same catalyst, under identical conditions for 28 hours, and after performing the chromatography, it was achieved 40 milligrams (6.5%) of the rearranged product 4 or 2(3)-methyl-6-[14-methoxy-14-oxo-drim-8(12)-en-11-il-methyl]-naphtho-1,4-quinone, a yellow oil, 170 milligrams of 5,8-dihydro-2(3)-methyl-6-[14-methoxy-14-oxo-drim-8(12)-en-11-il-methyl]-naphtho-1,4-quinone or compound 5, a reddish oil and further 298 milligrams (48%) of 5,8-dihydro-2(3)-methyl-6-[14-methoxy-14-oxo-drim-8(12)-en-11-il-methyl]-naphthalene-1,4-diol or compound 6, a brown solid of melting point 97° C. Acetylation of compound 6, under standard conditions, leads to compound 6a or 5,8-dihydro-2(3)-methyl-6-[14-methoxy-14-oxo-drim-8(12)-en-11-il-methyl]-naphthalene-1,4-diol diacetate.

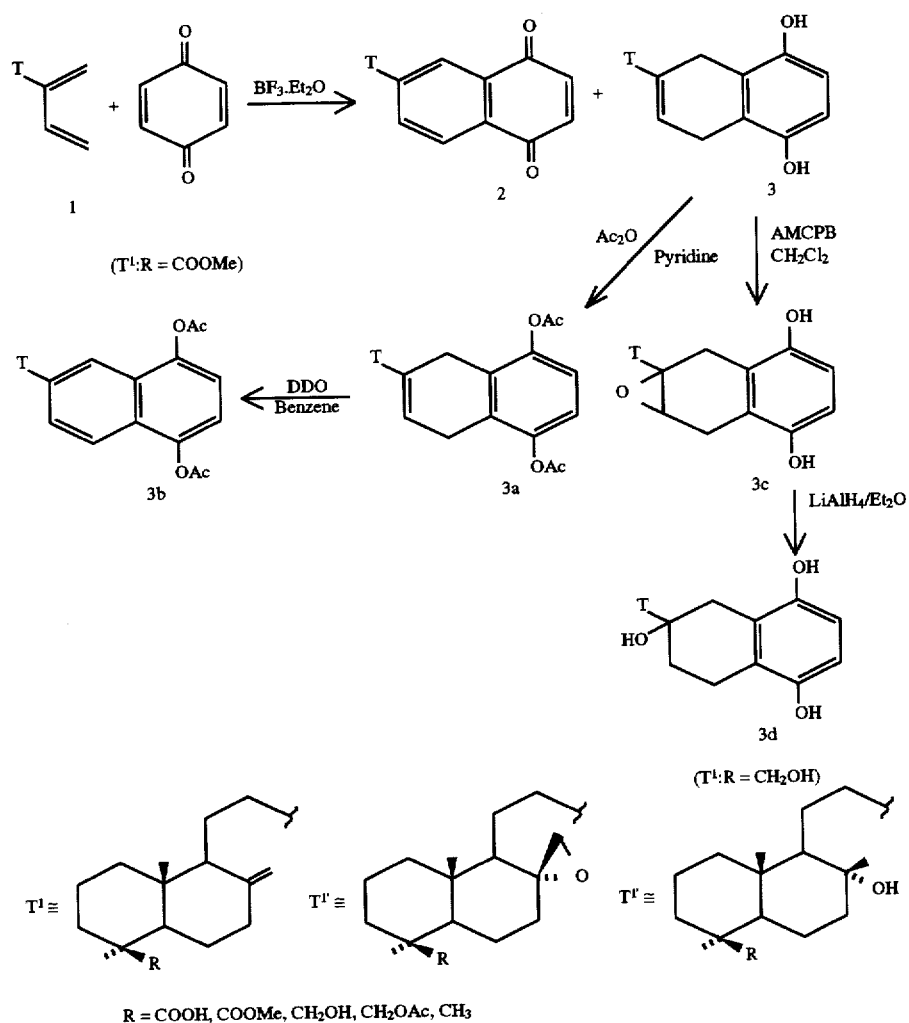

Third Example

From 200 milligrams or 0.63 milliMole of methyl trans-comunate or reacting compound 7 and 68 milligrams or 0.63 milliMole of p-benzoquinone, with the same catalyst, conditions and operations than in the first example, and after performing the chromatography, a high portion of the product having not reacted is recovered and it is obtained 95 milligrams (23%) of compound 8 or 4a,5,8,8a-tetrahydro-6-methyl-5-[14-methoxy-14-oxo-drim-8(12)-en-11-il-methyl]-naphthalene-1,4-quinone, a yellow oily product, and traces of compound 9 which was acetylated up to yield compound 9a.

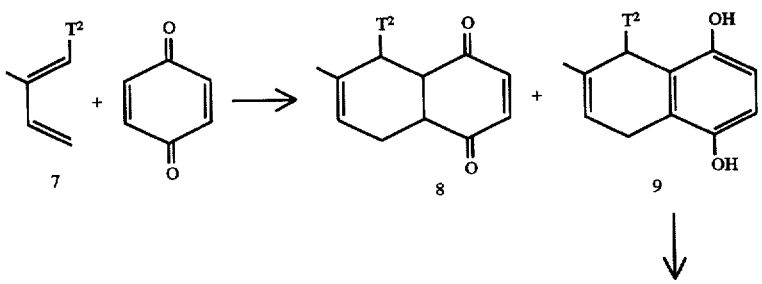

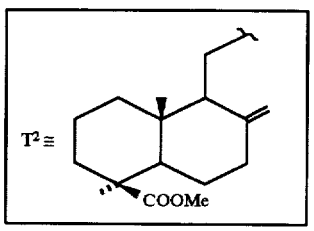

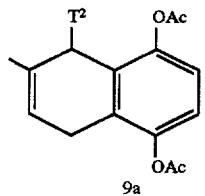

Fourth Example

From 1 gram or 7.35 milliMole of mircene or compound 10 in 150 milliliters of anhydrous ether and 0.78 grams or 7.35 milliMole of p-benzoquinone, in the presence of a small amount of $BF_3$-etherate, the reaction being kept under the same fore conditions, for 36 hours and operating as described in the first example, 1.65 grams of a reddish viscous residue are obtained, from which it is isolated, by chromatography on silica-gel, 150 milligrams (8.5%) of compound 11, or 6-(4-methylpent-3-enil)-naphtho-1,4 -quinone, a yellow-orange coloured oily product, 300 milligrams (17%) of compound 12 or 5,8-dihydro-6-(4-methylpent-3-enil )-naphtho-1,4-quinone with a similar constitution and appearance and 825 milligrams (46%) of compound 13 or 5,8-dihydro-6-(4-methylpent-3-enil)-naphthalene-1,4-diol, a brown-reddish solid of melting point 120° C. Acetylation of compound 13 leads, under standard conditions, to compound 13a or 5,8-dihydro-6-(4-methylpent-3-enil)-naphthalene-1,4-diol diacetate in a yield of 75% after purifying. Next, 198 milligrams or 0.6 milliMole of compound 13a will be dissolved into 50 milliliters of dichloromethane, and 110 milligrams or 0.6 milliMole of metachloroperbenzoic acid (mcpba) and 150 milligrams or 2 milliMole of sodium hydrocarbonate are added. Mixture is kept under dry atmosphere and on stirring for 30 minutes. Reaction is finished by washing the organic phase with a solution of $Na_2SO_4$ in water untill complete reduction of the excess oxidizing agent, it is subsequently washed with water up to neutralization, dried, filtered and distilled, so originating 153 milligrams of a colourless oily residue, which once subjected to chromatography, yields 120 milligrams (58%) of compound 14 or 5,8-dihydro-6-(3,4-epoxy-4-nethylpentil)naphthalene-1,4-diol diacetate.

Biological Activity

Cytotoxic activity of terpene-quinones obtained has been determined by a simple screening procedure using an adapted form from method described by Bergeron et al. (1984) against cell cultures P-388 (suspension culture of DBA/2 mouse lymphoid neoplasm), A-549 (single-layer culture of human lung carcinoma), HT-19 (single-layer culture of human colon carcinoma) and MEL-28 (single-layer culture of human melanoma). The values of $IC_{50}$ in microM., observed for representative compounds mentioned on this work, are listed in the following table, in which there are also included the values found for avarone, as an element for comparison.

| Compound | P-388 | A-549 | HT-29 | MEL-28 |
|---|---|---|---|---|
| Avarone | 3.1 | 6 | 6 | 6 |
| 2 | 0.12 | 0.23 | 0.23 | 0.23 |
| 3 | 0.23 | 0.28 | 0.28 | 0.28 |
| 3a | 0.24 | 0.24 | 0.5 | 0.5 |
| 3b | 0.2 | 0.2 | 1 | 0.2 |
| 3c | 0.3 | 1.1 | 1.1 | 0.6 |
| 4 | 1.1 | 1.1 | 2.3 | 2.3 |
| 5 | 0.58 | 1.2 | 2.3 | 1.2 |
| 8 | 1.2 | 2.3 | 2.3 | 2.3 |
| 12 | 1.0 | 2.1 | 2.1 | 2.1 |
| 13 | 2.1 | 5.9 | 5.9 | 5.9 |
| 14 | 1.4 | 7.0 | 7.0 | 7.0 |

P-388 cells are sown into 16 millimeters wells at 1×10,000 cells per well in alliquots of 1 millilitre of MEM 5FCS containing the indicated drug concentration. Separately, a batch of drug-less cultures is sown as a control for growth to assure that cells are kept at a logarithmic growth stage. All determinations are made in duplicate. After three days of incubation at 37° C., 10% $CO_2$ in a 98% humidity

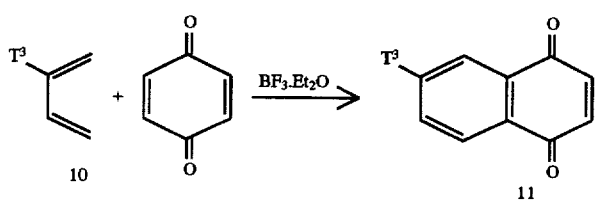

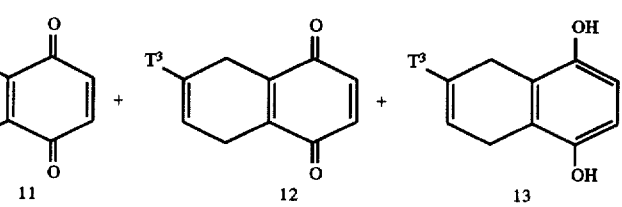

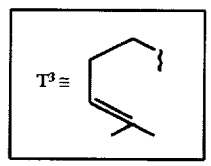

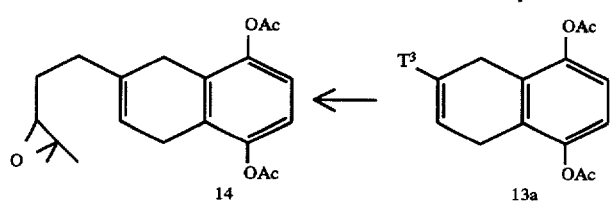

We claim:

1. A compound of the formula:

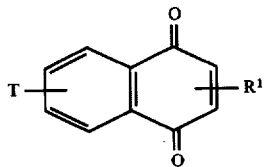

wherein $R^1$ is selected from the group consisting of hydrogen, alkyl, alkoxy, alkylamine and dialkylamine; and wherein and T is either an alkyl or a cycloalkyl group containing one or more isoprene units.

2. A compound of claim 1, wherein T comprises an isoprene, monoterpene, or sesquiterpene group.

3. A compound of the formula:

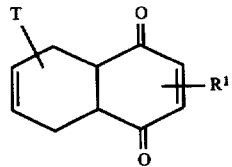

wherein $R^1$ is selected from the group consisting of hydrogen, alkyl, alkoxy, alkylamine and dialkylamine; and wherein and T is either an alkyl or a cycloalkyl group containing one or more isoprene units.

4. A compound of claim 3, wherein T comprises an isoprene, monoterpene, or sesquiterpene group.

5. A compound of the formula:

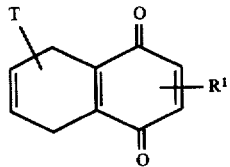

wherein $R^1$ is selected from the group consisting of hydrogen, alkyl, alkoxy, alkylamine and dialkylamine; and wherein and T is either an alkyl or a cycloalkyl group containing one or more isoprene units.

6. A compound of claim 5, wherein T comprises an isoprene, monoterpene, or sesquiterpene group.

7. A compound of the formula:

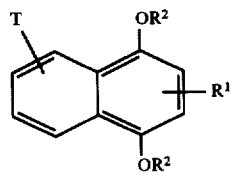

wherein $R^1$ and $R^2$ are each independently selected from the group consisting of hydrogen, alkyl, alkoxy, alkylamine and dialkylamine; and wherein and T is either an alkyl or a cycloalkyl group containing one or more isoprene units.

8. A compound of claim 7, wherein T comprises an isoprene, monoterpene, or sesquiterpene group.

9. A compound of the formula:

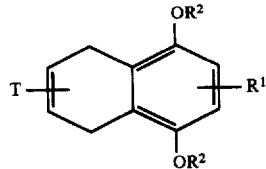

wherein $R^1$ and $R^2$ are each independently selected from the group consisting of hydrogen, alkyl, alkoxy, alkylamine and dialkylamine; and wherein and T is either an alkyl or a cycloalkyl group containing one or more isoprene units.

10. A compound of claim 9, wherein T comprises an isoprene, monoterpene, or sesquiterpene group.

11. The compound 6-[14-methoxy-14-oxo-drim-8(12)-en-11-il-methyl]-naphtho-1,4-quinone.

12. The compound 5,8-dihydro-6-[14-methoxy- 14-oxo-drim-8(12)-en-11-il-methyl]-naphthalele-1,4-diol.

13. The compound 5,8-dihydro-6-[14-methoxy-14-oxo-drim-8(12)-en-11-il-methyl]-naphthalele-1,4-diol diacetate.

14. The compound 2(3)-methyl-6-[14-methoxy-14-oxo-drim-8(12)-en-11-il-methyl]-naphtho-1,4-quinone.

15. The compound 5,8,-dihydro-2(3)-methyl-6-[14-methoxy-14-oxo-drim-8(12)-en-11-il-methyl]-naphtho-1,4-quinone.

16. The compound 5,8-dihydro-2(3)-methyl-6-[14-methoxy-14-oxo-drim-8(12)-en-il-methyl]-naphthalene-1,4-diol.

17. The compound 5,8-dihydro-2(3)-methyl-6-[14-methoxy-14-oxo-drim-8(12)-en-il-methyl]-naphthalene-1,4-diol diacetate.

18. The compound 4a,5,8,8a-tetrahydro-6-methyl-5-[14-methoxy-14-oxo-drim-8(12)-en-il-methyl]-naphthalene-1,4-quinone.

19. The compound 6-(4-methylpent-3-enil)-naphto-1,4-quinone.

20. The compound 5,8-dihydro-6-(4-methylpent-3-enil)-naphtho-1,4-quinone.

21. The compound 5,8-dihydro-6-(4-methylpent-3-enil)-naphthalene-1,4-diol.

22. The compound 5,8-dihydro-6-(4-methylpent-3-enil)-naphthalene-1,4-diol diacetate.

23. The compound 5,8-dihydro-6-(3,4-epoxy-4-methylpentil)-naphthalene-1,4-diol diacetate.

24. The compound 6-[14-methoxy-14-oxo-drim-8,(12)-epoxi-11-yl-methyl]-naphthalene-1,4-diol diacetate.

25. 6-[14-methoxy-14-oxo-drim-8(12)-en-11-yl-methyl]-naphthalene-1,4-diol diacetate.

26. 5,8-dihydro-6-epoxi-6-[14-oxo-drim-8-oxo- 11-yl-methyl]-naphthalene-1,4-diol.

27. 2(3)-methyl-5-[14-methoxy-14-oxo-drim-8(12)-en-yl-methyl]-naphtho-1,4-quinone.

* * * * *